United States Patent

Grögler et al.

Patent Number: 4,521,338
Date of Patent: Jun. 4, 1985

[54] PROCESS FOR THE PREPARATION OF LOW MOLECULAR WEIGHT 4,4′-DIPHENYLMETHANE-URETDIONE-DIISOCYANATES

[75] Inventors: Gerhard Grögler, Leverkusen; Richard Kopp, Cologne, both of Fed. Rep. of Germany

[73] Assignee: Bayer Aktiengesellschaft, Leverkusen, Fed. Rep. of Germany

[21] Appl. No.: 404,106

[22] Filed: Aug. 2, 1982

[30] Foreign Application Priority Data

Aug. 12, 1981 [DE] Fed. Rep. of Germany ....... 3131779

[51] Int. Cl.$^3$ ............................................. C07D 229/00
[52] U.S. Cl. ................................................. 260/239 A
[58] Field of Search .................................. 260/239 AR

[56] References Cited

U.S. PATENT DOCUMENTS

| | | | |
|---|---|---|---|
| 2,683,144 | 7/1954 | Balon et al. | 260/239 A |
| 3,290,288 | 12/1966 | Oertel et al. | 260/239 A |
| 3,919,195 | 11/1975 | Bakhitov et al. | 260/239 A |
| 3,993,641 | 11/1976 | Tiemann et al. | 260/239 A |
| 4,022,752 | 5/1977 | Horn et al. | 524/98 |

FOREIGN PATENT DOCUMENTS 821158 9/1959 United Kingdom.
1207673 10/1970 United Kingdom.

OTHER PUBLICATIONS

J. Org. Chem. 8 23, 1943.

Primary Examiner—Donald G. Daus
Assistant Examiner—William A. Teoli, Jr.
Attorney, Agent, or Firm—Gene Harsh; Joseph C. Gil; Lyndanne M. Whalen

[57] ABSTRACT

Low molecular weight 4,4′-diphenylmethane-uretdione-diisocyanates corresponding to the formula:

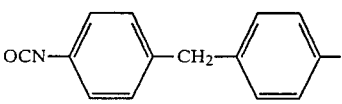

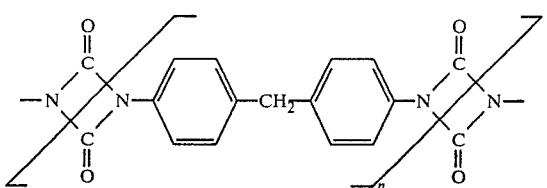

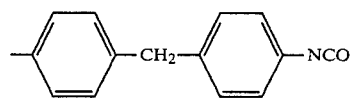

wherein
n is a number from 0 to 1, are made by dimerizing diphenylmethane-4,4′-diisocyanate at a temperature of 50° C. or less in a mixture of non-polar and moderately polar solvents in the presence of a dimerization catalyst. The dimerization product may then be worked up at low temperatures (i.e., ≦50° C.). The dimerization products of diphenylmethane-diisocyanate thus obtained generally have only a small amount of oligomeric uretdione-diisocyanates present. These dimerization products may be used advantageously in the synthesis of polyurethanes.

20 Claims, No Drawings

PROCESS FOR THE PREPARATION OF LOW MOLECULAR WEIGHT 4,4'-DIPHENYLMETHANE-URETDIONE-DIISOCYANATES

BACKGROUND OF THE INVENTION

This invention relates to a process for the preparation of low molecular weight 4,4'-diphenylmethane-uretdione-diisocyanates corresponding to the formula:

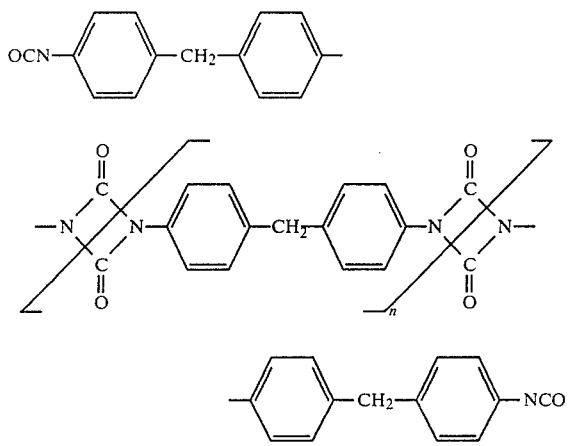

in which
n represents 0 to 1, preferably 0 to 0.5.

Aromatic uretdione-diisocyanates ("dimeric" diisocyanates) and processes for the production thereof are known. See "Kunststoff-Handbuch", Volume VII, Polyurethane, published by Vieweg-Höchtlen, Carl-Hanser-Verlag, Munich, 1966.

Materials which have been described as dimerization catalysts useful in such processes include: trialkylphosphines (J. Org. Chem.8, 23 (1943)); aromatic-aliphatic tertiary phosphines; alkyl-diaryl phosphines (German Auslegeschrift No. 2,452,390); tri- or tetra- substituted pyridines (British Pat. No. 821,158); trialkyl phosphites (German Auslegeschrift No. 2,349,726) and phosphorous acid-tris-dialkylamides (U.S. Pat. No. 3,290,288). In some cases, the dimerization reaction to form the uretdione may take place in bulk. However, solvents which are inert to NCO groups are generally used. Examples of solvents described as suitable for such processes include: benzene, toluene, xylene, chlorobenzene, nitrobenzene, acetone, methylethylketone, acetic ester, dioxane, tetrahydrofuran, aliphatic hydrocarbons, dimethylformamide and methylene chloride. No distinction between these solvents (with respect to polarity or dissolving power) has been made in the literature.

The fact that undesirable by-products (for example, isocyanurate) may be produced during the dimerization of aromatic isocyanates where reactive dimerization catalysts are used was recognized in U.S. Pat. No. 2,683,144. To minimize formation of such by-products, it is recommended that dimerization be interrupted when the required dimerization stage has been reached. Alkylation agents (e.g., cyclohexane sulphonic acid methylester or benzyl chloride) are used as inhibitors (stoppers) for the dimerization catalyst.

The literature teaches that aromatic diisocyanates which are substituted by other radicals R (for example, alkyl groups) in one or both ortho-positions relative to an NCO group, produce uretdione-diisocyanates having double the molecular weight of the starting compounds. An example of one such compound is the dimeric toluylene diisocyanate:

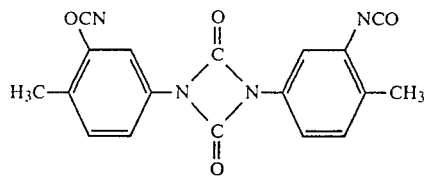

This teaching has been extended in the patent literature to aromatic diisocyanates in which the ortho-position (relative to the aromatically bound NCO group) has only H atoms. The conventional term for such uretdione-diisocyanates is a "diphenylmethane-diisocyanate-dimer". The diphenylmethane-diisocyanate-dimer based on 4,4'-diphenylmethane-diisocyanate was believed to be generally represented by the formula:

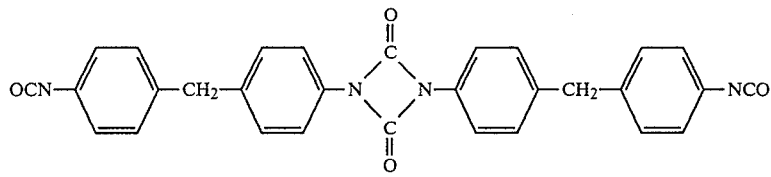

German Auslegeschrift No. 1,445,721 (U.S. Pat. No. 3,290,288), however, teaches that in addition to dimeric uretdiones during the dimerization of diphenylmethane-diisocyanate, tri-, tetra- and pentameric uretdiones are produced. These compounds are represented by the formula:

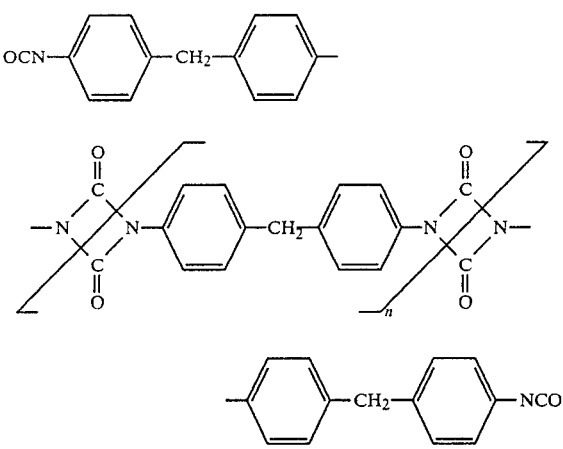

in which
n=0 to 5.

German Auslegeschrift No. 2,419,968 discloses that the dimerized diphenylmethane-diisocyanates described in the literature may be used in the synthesis of high molecular weight polyurethanes having uretdione groups by a reaction in highly-polar solvents such as DMF. However, as the degree of polydimerization increases (n slightly greater than 2.5), the reacvitity with H-acid compounds decreases due to increasingly difficult solubility of the uretdione-diisocyanates. Consequently, such higher molecular weight oligomers are not suitable for many polyurethane reactions, particularly those which are carried out in the absence of solvent or at a temperature below the melting points of the uretdione-diisocyanates.

The significance of the solvent present during the dimerization reaction has not been discussed very often in the patent literature. More particularly, the influence of the solvent during the dimerization of aromatic diisocyanates in which the NCO group is flanked only by H-atoms in the ortho-positions has not been specifically considered. Some inert solvents which are described in the literature as suitable for the dimerization of aromatic isocyanates have been found to be useless in the dimerization of diphenylmethane-diisocyanate because high molecular weight MDI dimer mixtures (in which n is much greater than 2.5) are produced. Such high molecular weight mixtures are generally not suitable for other polyurethane reactions (see Example 1).

It has also been found that poly-dimers are produced almost exclusively in very highly polar solvents (such as in dimethylformamide or dimethylacetamide). Such poly-dimers are different in reactivity and convertibility from the low molecular weight compounds of the present invention.

SUMMARY OF THE INVENTION

It is an object of the present invention to provide a process for the production of low molecular weight 4,4'-diphenylmethane-uretdione-diisocyanates.

It is also an object of the present invention to provide a process for the production of uretdione-diisocyanates based on 4,4'-diphenylmethane-diisocyanate having a low degree of oligomerization which may be employed as a reactant in a polyaddition reaction.

It is another object of the present invention to provide a process for the production of a diphenylmethane-uretdione-diisocyanate which is substantially uniform in structure in high yields.

These and other objects which will be apparent to those skilled in the art are accomplished by dimerizing a 4,4'-diphenylmethane-diisocyanate at a temperature less than 50° C. in the presence of a catalyst. The dimerization reaction must be carried out in a mixture of non-polar and moderately polar solvents. The non-polar solvent is generally one in which the diisocyanate starting material has a solubility of from 5 to 25 wt. %. The product of this dimerization corresponds to the formula:

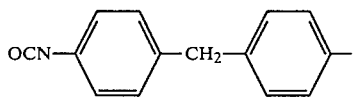

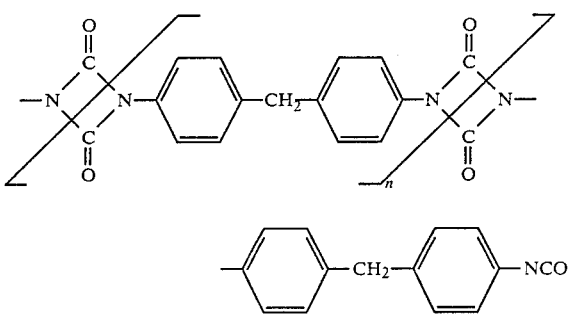

in which n represents a number from 0 to 1, preferably 0 to 0.5.

Surprisingly, it has been found that the choice or the quantity of the catalyst within the conventional limits, or the controlled stopping of the catalyst at a specific degree of dimerization does not result in selective formation of diphenylmethane-uretdione-diisocyanates having a low molecular weight. It has also been found that the particular solvent, use of as low a dimerization temperature as possible and particularly, use of a low working-up temperature during isolation of the dimers are crucial to selective formation of diphenylmethane-uretdione-diisocyanates.

The dimerization of diphenylmethane-4,4'-diisocyanate in a mixture of non-polar and polar solvents as required in the present invention yields diphenylmethane-uretdione-diisocyanates having a very low degree of polyaddition (i.e., n in the above-described formula is such that $n \leq 1$, preferably $\leq 0.5$). The degree of polyaddition is particularly low when the non-polar solvent is one in which the diphenylmethane-4,4'-diisocyanate is not highly soluble (i.e., only from 5 to 25 wt. %, preferably from 5 to 15 wt. % of diisocyanate will dissolve in the solvent). If the dimerization of the diphenylmethane-diisocyanate is carried out only in such a non-polar solvent, low molecular weight diphenylmethane-uretdione-diisocyanates are obtained, however, such diphenylmethane-uretdione-diisocyanates still contain a relatively large quantity of monomeric diphenylmethane-diisocyanate starting components. Further, use of only the non-polar solvent is not economically advantageous due to considerable dilution of the product.

As a result of adding a suitable, moderately polar NCO-inert solvent to the non-polar solvent, the solubility of diphenylmethane-diisocyanate in the solvent mixture may be increased without affecting the formation of the low molecular weight diphenylmethane-uretdione-diisocyanate. During such a dimerization process in which both non-polar and moderately polar solvents are employed, the initially formed diphenylmethane-uretdione-diisocyanate ($n \geq 0$) precipitates and does not oligomerize further to any significant extent.

The present invention relates to a process for the production of low molecular weight 4,4'-diphenylmethane-uretdione-diisocyanates corresponding to the formula:

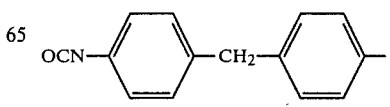

-continued

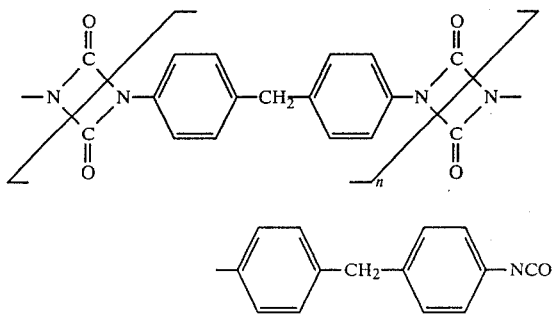

in which n represents a number from 0 to 1, preferably 0 to 0.5. These compounds are prepared by dimerizing diphenylmethane-4,4'-diisocyanate in a mixture of non-polar and moderately polar solvents in the presence of dimerization catalysts and optionally inhibitors. The solubility of the diphenylmethane-4,4'-diisocyanate in the non-polar solvent should be from 5 to 25 wt. %, preferably from 5 to 15 wt. %. The temperature during the dimerization reaction and during isolation of the uretdione-diisocyanates should be maintained below 50° C., preferably below 30° C.

The process of the present invention is particularly advantageous in that the substantially uniform diphenylmethane-uretdione-diisocyanate (n≦1, preferably ≦0.5) is obtained in very high yields (from 90 to 98% of the theoretical yield).

The catalysts useful in the process of the present invention include those described above and other dimerization catalysts known to those skilled in the art. Trialkyl phosphines, such as triethyl phosphine and tributyl phosphine are particularly preferred catalysts. These catalysts may be used in quantities from 0.05 to 5 wt. %, preferably from 0.1 to 1.0 wt. % and most preferably from 0.1 to 0.35 wt. %.

Suitable "non-polar" solvents for the present invention include: aliphatic and/or cycloaliphatic hydrocarbons, such as hexane, octane, cyclopentane, cyclohexane, cyclododecane; and corresponding hydrocarbon distillates having a predominant quantity of aliphatic and/or cycloaliphatic hydrocarbons, for example, petroleum ether, petroleum naphtha or ligroin. The dielectric constant of such solvents is generally below 2.10. Hydrocarbon distillates such as petroleum ether, ligroin and light petrol are particularly preferred non-polar solvents.

Aromatic hydrocarbons, optionally the chlorinated derivatives thereof, carboxylic acid esters, ketones and ethers are "moderately polar" solvents which may be used in the process of the present invention. The dielectric constants of these solvents is from about 2.24 to 10, but may be higher (up to about 22) in the case of a ketone. Examples of such moderately polar solvents include: benzene, toluene, xylene, chlorobenzene, acetic acid methyl ester, acetic acid ethyl ester, propionic acid diethyl ester, formic acid diethyl ester, phthalic acid diethyl ester, phthalic acid dioctyl ester, acetone, methylethylketone, cyclohexanone, isophorone, diethylether, tetrahydrofuran and carbon tetrachloride. Aromatic hydrocarbons, in particular toluene, are preferred.

The ratio of non-polar to moderately polar solvent depends upon the solubility of diphenylmethane-diisocyanate in this solvent mixture. The solvent mixtures are generally such that the ratio of non-polar to moderately polar solvent is from 2:1 to 1:2, preferably about 1:1.

The process of the present invention may be carried out by stirring from 1 to 2 parts by weight of non-polar solvent (at room temperature) with 1 part by weight of diphenylmethane-diisocyanate until the saturation point is reached. Then just enough polar solvent is added to form a homogeneous solution. The concentration of diphenylmethane-diisocyanate in such a solvent mixture generally amounts to from 25 to 60 wt. %, preferably from 30 to 50 wt. %.

A highly-concentrated solution of diphenylmethane-diisocyanate in the moderately polar solvent may also be mixed with the non-polar solvent.

The dimerization reaction conditions, such as choice and quantity of catalyst, reaction times and stopping the action of the catalyst have been described in detail in the literature. However, the literature does not teach that during the dimerization reaction, the reaction temperatures should not be allowed to rise to any great extent (i.e., the temperature should be maintained at ≦50° C., preferably ≦30° C.). It is generally advisable to stop the action of the catalyst after reaching the required dimerization and/or oligomerization stages in accordance with techniques known to those in the art.

It is also important that during processing of the dimer the temperature be kept relatively low to prevent further reaction of the uretdione with the free NCO groups of the dimers to form polymeric uretdiones. Polymeric uretdiones are not readily soluble, contain only a few free NCO groups and may be further reacted only with great difficulty.

The dimers or low molecular weight oligomers made in accordance with the present invention (n≦1) may advantageously be used in their low molecular weight or low oligomeric form for the synthesis of polyurethane systems. They are particularly useful for the production of one-component reactive systems such as those described in our pending patent application Ser. No. 404,010 filed: 8/2/82, now U.S. Pat. No. 4,442,280.

Having thus described our invention, the following examples are given by way of illustration. All parts and percentages given in these examples are parts by weight and percents by weight, unless otherwise indicated.

EXAMPLES

Example 1

(1a) Preparation of "dimeric" diphenylmethane diisocyanate according to known methods 1.5 g of tributyl phosphine were added at room temperature to a solution of 1,000 g (4.0 mols) of diphenylmethane-4,4'-diisocyanate (MDI) in 2,000 g of toluene. After a short time, the dimeric MDI separated out of the solution and the temperature gradually rose to from 30° to 35° C. The reaction mixture was stirred for an additional 4 hours and the dimerization catalyst was then stopped by adding 1.5 g of toluene sulfonic acid methyl ester. The solid MDI "dimer" which formed was filtered by suction. After drying for about 5 hours at from 70° to 80° C., about 800 g of MDI "dimer" were obtained in the form of a fine powder. This powder was insoluble in practically all solvents. The decomposition point was above 250° C.

Conventional titration of free NCO groups in acetone or dimethylformamide using dibutylamine, particularly in the case of a high molecular weight MDI dimer results in very inaccurate values due to formation of insoluble residues and separation of the uretdione ring. Therefore, the free NCO content was determined by a reaction with dibenzylamine as sterically hindered amine and gravimetrically determining the quantity of amine which was absorbed. This determination was made in the following manner.

A suspension of 10 g of MDI dimer in 150 ml of toluene and 15 g of dibenzylamine (excess) were heated at 50° C. for 30 minutes. The solid product was then isolated and the increase in weight was determined. With a defined addition product of 2 mols of sterically hindered amine to 1 mol of the MDI "dimer", different amine absorptions resulted where there were different degress of polyaddition of the MDI dimer (=n). The NCO content and the value of n, or the molecular weight, could be calculated from the dibenzylamine absorption by MDI dimer (see Table I).

TABLE I

| n | Molecular weight | Amine absorption g/10 g MDI-dimer | % NCO (calculated) |
|---|---|---|---|
| 0 | 500 | 7.88 | 16.8 |
| 1 | 750 | 5.26 | 11.2 |
| 2 | 1000 | 3.94 | 8.4 |
| 3 | 1250 | 3.15 | 6.7 |
| 4 | 1500 | 2.62 | 5.6 |

The "MDI dimer" prepared according to the above preparation method showed an amine absorption of 3.0 g per 10 g of MDI dimer, corresponding to a calculated NCO of 6.4%. A so-called MDI "dimer" of this type is unsuitable for the intended polyurethane reactions (n greater than 3).

Surprisingly, the NCO groups of the di- and oligomeric MDI-uretdione-diisocyanate could also be determined with sufficient accuracy using the sterically hindered diamine 2,4-diamino-3,5-diethyl-toluene. During this operation, $NH_2$-terminated polyureas were produced having a uretdione ring which was still intact. In the case of low molecular weight MDI dimer, the amine absorption (reaction with free NCO groups) was highest.

(1b) Preparation of suitable dimers according to the present invention, or of diphenylmethane-uretdione-diisocyanates which have low oligomer values Dimerization was carried out in accordance with the procedure described in Example (1a), with the exception that the raw product was washed with petroleum ether after being filtered under suction and was then dried under vacuum at low temperatures up to about 30° C. In this manner, a low molecular weight uretdione-diisocyanate was obtained. The product diisocyanate had an amine absorption of 7.2 g which corresponds to a calculated NCO value of 15.3%, i.e. a value of n=0.2. In contrast to the highly-oligomerized MDI derivative produced in Example (1a), this diisocyanate which was substantially a true dimer would be suitable for the production of highly-elastic polyurethanes.

(1c) Comparison of different solvents with respect to the dimerization reaction 0.25 g of tributyl phosphine were added to a solution of 100 g of diphenylmethane-4,4'-diisocyanate in 100 g in each of the solvents specified in Table II. After a short period of time, the dimer separated in the form of a white deposit. The mixture was stirred for an additional 2 hours at room temperature and the dimerization catalyst was then stopped by adding 0.25 of toluene sulfonic acid methyl ester. The MDI dimer was filtered under suction and, after being washed with petroleum ether, was dried under vaccum at room temperature without heating.

Table II shows the yields (% of the theoretical yield), the absorbed quantity of sterically hindered amine per 10 g of dimer (see Example 1a)) and the NCO content of the dimer, or of the oligomers n, calculated therefrom.

TABLE II

| Solvent | MDI dimer yield (% of the theoretical yield) | Amine absorption (g/10 g MDI-dimer) | Average molecular weight | % NCO (calculated) | n (calculated) |
|---|---|---|---|---|---|
| A. Tetrahydrofuran | 55 | 3.3 | 1175 | 7.1 | 2.7 |
| B. Dioxane | 50 | 1.7 |  | 3.54 | 7.5 |
| C. Chloroform | 90 | 3.0 |  | 6.4 | 3.3 |
| D. Methylene chloride | 88 | 3.0 |  | 6.4 | 3.3 |
| E. Dichloroethane-1,2 | 92 | 4.4 | 900 | 9.4 | 1.6 |
| F. Toluene | 79 | 7.20 | 550 | 15.3 | 0.20 |
| G. Acetic ester | 62 | 7.49 | 525 | 16.0 | 0.10 |
| H. Acetone | 75 | 7.44 | 530 | 15.85 | 0.12 |
| I. Chlorobenzene | 75 | 7.44 | 530 | 15.85 | 0.12 |
| J. Benzoic acid ethyl ester | 80 | 7.20 | 550 | 15.3 | 0.2 |
| K. Phthalic acid dioctyl ester | 72 | 6.70 | 588 | 14.3 | 0.35 |

It can be seen from the results presented in Table II that under the above-described reaction conditions, high molecular weight diphenylmethane-uretdiones are obtained in a strongly polar solvent (Experiments A–D). Such high molecular weight compounds are of limited usefulness at best for specific polyurethane reactions. Products such as that produced in Experiment E produce only relatively flexible elastomers, but they may still be used.

The products of Experiments F through K were low molecular weight oligomers (n≦1) and would be suitable for other polyurethane reactions. However, if these MDI uretdiones are tempered for some time at 100° C., then a further reaction takes place at the NCO groups which are still free, forming high molecular weight MDI dimer (See Example 3).

Example 2

100 g of the non-polar solvents listed in Table III were added in each case to a solution of 100 g of MDI in 100 g of toluene. 0.25 g of tributyl phosphine were then stirred into the homogeneous solution. After a short time, the low molecular weight diphenylmethane-uretdione-diisocyanate (MDI dimer) separated in the form of a white deposit. The mixture was stirred for an additional 2 hours at room temperature, then filtered under suction. The MDI dimer was dried with the exclusion of moisture under vacuum at room temperature after it had been washed with petroleum ether. Table III specifies the yield (% of the theoretical yield), the quantity of dibenzylamine absorbed per 10 g of MDI dimer, and the NCO content of the MDI dimer calculated therefrom.

TABLE III

| Non-polar solvent | MDI dimer yield (% of the theoretical yield) | Amine absorption/10 g of MDI dimer | NCO Calculated | Molecular weight | n |
|---|---|---|---|---|---|
| A. Ligroin | 92 | 7.52 | 16.1 | 522 | 0.09 |
| B. Petroleum naphtha | 95 | 7.2 | 15.3 | 549 | 0.2 |
| C. Light petrol | 90 | 7.89 | 16.7 | 503 | 0.012 |
| D. Cyclohexane | 96 | 7.60 | 16.3 | 515 | 0.06 |
| E. Hexane | 90 | 7.75 | 16.5 | 509 | 0.04 |
| F. Petroleum ether | 97 | 7.88 | 16.8 | 500 | 0.0 |

Where n=0, the calculated amine absorption was 7.88 g/10 g of MDI dimer.

Thus, very low oligomeric uretdiones of diphenylmethane-4,4'-uretdione-diisocyanate were obtained in an excellent yield when made by the process of the present invention.

Similarly favorable results were obtained when acetic ester was used instead of toluene as a moderately polar medium with the same proportion of non-polar solvent (petroleum ether).

Example 3

Influence of the temperature conditions on the low molecular weight MDI dimer of Example 2

The MDI dimer obtained from ligroin in Example 2 was tempered at 100° C. for different periods of time. Higher molecular weight products were obtained after the times specified in Table IV.

TABLE IV

| | Time (min.) | Amine absorption g/10 g of MDI dimer | NCO calculated (%) | n calculated | average molecular weight |
|---|---|---|---|---|---|
| A. | 0 | 7.2 | 15.3 | 0.2 | 550 |
| B. | 15 | 6.42 | 13.4 | 0.51 | 627 |
| C. | 30 | 6.75 | 12.1 | 0.77 | 692 |
| D. | 45 | 5.2 | 11.1 | 1.03 | 757 |
| E. | 60 | 3.65 | 7.8 | 2.3 | 1075 |
| F. | 120 | 0.22 | 0.5 | 65 | high molecular weight (~17000) |

However, when stored at 25° C., the initial product (n=0.12) remained practically unchanged for three months.

What is claimed is:

1. A process for the production of a low molecular weight 4,4'-diphenylmethane-uretdione-diisocyanate corresponding to the formula:

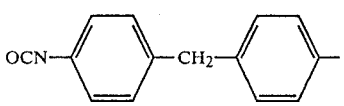

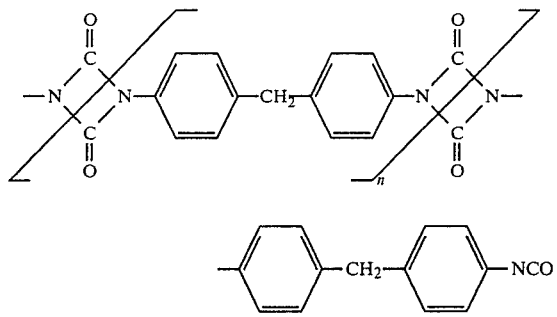

in which n represents a number from 0 to 1, comprising dimerizing a 4,4'-diphenylmethane-diisocyanate at a temperature less than 50° C. in the presence of a catalyst and in an isocyanate-inert solvent-mixture of non-polar and moderately polar solvents.

2. The process of claim 1 wherein the solubility of the 4,4'-diphenylmethane-diisocyanate in the non-polar solvent is from 5 to 25 wt. %.

3. The process of claim 1 wherein n represents a number from 0 to 0.5.

4. The process of claim 1 wherein the non-polar and moderately polar solvents are used in quantities such that the ratio of non-polar to moderately polar solvent is from 1:2 to 2:1.

5. The process of claim 4 wherein the non-polar solvent is an aliphatic and/or cycloaliphatic hydrocarbon and the moderately polar solvent is selected from the group consisting of aromatic hydrocarbons, chlorinated derivatives of aromatic hydrocarbons, carboxylic acid esters, ketones, ethers and mixtures thereof.

6. The process of claim 1 wherein the non-polar solvent is an aliphatic and/or cycloaliphatic hydrocarbon.

7. The process of claim 1 wherein the moderately polar solvent is a compound selected from the group consisting of aromatic hydrocarbons, chlorinated derivatives of aromatic hydrocarbons, carboxylic acid esters, ketones, ethers and mixtures thereof.

8. The process of claim 1 wherein the solubility of the 4,4'-diphenylmethane-diisocyanate in the non-polar solvent is from 5 to 15 wt. % at room temperature and the dielectric constant of the non-polar solvent is below 2.10.

9. The process of claim 8 wherein the dielectric constant of the moderately polar solvent is from 2.24 to 10.

10. The process of claim 1 wherein the dielectric constant of the moderately polar solvent is from 2.24 to 10.

11. The process of claim 1 wherein the moderately polar solvent is a ketone having a dielectric constant up to 22.

12. The process of claim 1 wherein the non-polar solvent is selected from the group consisting of petroleum ether, ligroin, petrol and mixtures thereof.

13. The process of claim 12 wherein the moderately polar solvent is toluene.

14. The process of claim 1 wherein the moderately polar solvent is toluene.

15. The process of claim 1 wherein the temperature is maintained below 30° C. during the dimerization reaction and any subsequent purification or separation.

16. The process of claim 1 wherein the catalyst is a trialkyl phosphine.

17. The process of claim 16 wherein the catalyst is employed in an amount which is from 0.1 to 1.0 wt. %.

18. The process of claim 1 wherein from 1 to 2 parts by weight of the non-polar solvent is stirred with one part of 4,4'-diphenylmethane-diisocyanate at room temperature up to the saturation point and then moderately polar solvent is added until a homogeneous solution is produced.

19. The process of claim 1 wherein the dimerization catalyst is tributyl phosphine.

20. The process of claim 1 wherein the product 4,4'-diphenylmethane-uretdione-diisocyanate is separated from any unreacted material or by-products at a temperature less than 50° C.

* * * * *